(12) United States Patent
Tranquillo et al.

(10) Patent No.: US 6,461,629 B1
(45) Date of Patent: Oct. 8, 2002

(54) METHOD OF NERVE REGENERATION USING BIOPOLYMER RODS WITH ORIENTED FIBRILS

(75) Inventors: Robert T. Tranquillo, Roseville, MN (US); Stefano Guido, Naples (IT)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/562,813

(22) Filed: May 1, 2000

Related U.S. Application Data (63) Continuation of application No. 08/725,916, filed on Oct. 4, 1996, now Pat. No. 6,057,137, which is a continuation-in-part of application No. 08/703,928, filed on Aug. 28, 1996, now Pat. No. 5,948,654, which is a continuation of application No. 08/319,291, filed on Oct. 6, 1994, now abandoned.

(51) Int. Cl.$^7$ .............................. A61F 2/00; A61F 2/04

(52) U.S. Cl. ..................... 424/422; 424/423; 424/426; 623/12

(58) Field of Search ....................... 606/152; 623/12; 424/422, 423, 426

(56) References Cited

U.S. PATENT DOCUMENTS

| | | | |
|---|---|---|---|
| 3,114,372 A | | 12/1963 | Griset, Jr. et al. |
| 4,018,906 A | | 4/1977 | Ostendorf |
| 4,485,096 A | | 11/1984 | Bell |
| 4,546,500 A | | 10/1985 | Bell |
| 4,835,102 A | | 5/1989 | Bell et al. |
| 4,837,379 A | | 6/1989 | Weinberg |
| 4,863,668 A | | 9/1989 | Griffiths et al. |
| 4,955,893 A | * | 9/1990 | Yannas et al. ............... 606/154 |
| 5,256,418 A | | 10/1993 | Kemp et al. |

FOREIGN PATENT DOCUMENTS

| WO | WO 89/10728 | 11/1989 |
|---|---|---|
| WO | WO 93/24155 | 12/1993 |
| WO | WO 95/20359 | 8/1995 |

OTHER PUBLICATIONS

Echizenya et al., "Mineralization and Biodegradation of CSF Shunting Systems", J. Neurosurgery 67 (4): 584–91 (1987).*
Azuma, T. et al., "A rheological approach to the architecture of arterial walls", *Japan J. Physiol.*, 21(1):27–47 (Feb. 1971).
Barocas, V. H. et al, "The fibroblast–populated collagen microsphere assay of cell traction force—Part 2: Measurement of the cell traction parameter", *Journal of Biomechanical Engineering*, 117:161–170 (May 1995).
Barocas, V. H. et al., "An anisotropic biphasic theory of tissue–equivalent mechanics: The interplay among cell traction, fibrillar network deformation, fibril alignment, and cell contact guidance", *Journal of Biomechanical Engineering* 119(2):137–145 (May 1997).
Barocas, V. H. et al., "Biphasic theory and in vitro assays of cell–fibril mechanical interactions in tissue–equivalent collagen gels", in *Cell Mechanics and Cellular Engineering*, ed. V. C. Mow, Springer–Verlag; pp. 185–209 (1994).
Bell, E. et al., "Production of a tissue–like structure by contraction of collagen lattices by human fibroblasts of different proliferative potential in vitro", *Proc. Natl. Acad. Sci. USA*, 76(3):1274–1278 (Mar. 1979).
Bergel, D. H., "The dynamic elastic properties of the arterial wall", *J. Physiol.* 156(3):458–469 (May 1961).
Burton, A., "Relation of structure to function of the tissues of the wall of blood vessels", *Physiol. Rev.*, 34(4):619–642 (Oct. 1954).
Buschmann, M. D. et al., "Chondrocytes in agarose culture synthesize a mechanically functional extracellular matrix", *J. Orthop. Res.*, 10(6):745–758 (1992).
Carr et al., "The Effect of Low Cycle Fatigue on a Novel Synthetic Collagen Vascular Graft" *Society for Biomaterials*, 20th Annual Meeting, Boxton, MA, p. 486 (Apr. 5–9, 1994).
Chen et al., "The Use of Collagen Polymer Tube and Fibrin Clot in Peripheral Nerve Repair", *Proceedings of the National Science Coundil, ROC*, 18(2):58–63 (Apr., 1994).
Dickinson, R. B. et al., "Biased cell migration of fibroblasts exhibiting contact guidance in oriented collagen gels", *Annals of Biomedical Engineering,*, 22(4):342–356 (1994).
Diglio, C. A. et al., "Rat cerebral microvascular smooth muscle cells in culture", *Journal of Cellular Physiology*, 129:131–141 (1986).
Dubuisson et al., "Sciatic Nerve Regeneration Across Gaps Within Collagen Chambers: The Influence of Epidermal Growth Factor", *Journal of Reconstructive Microsurgery*, 9(5):341–347 (Sep., 1993).
Flinn, R. A. et al. (Eds.), *Engineering Materials and Their Applications*, 3d Ed., pp. 75–78; Houghton Mifflin Company, Boston, Publ. (1986).

(List continued on next page.)

Primary Examiner—Sandra Saucier
(74) Attorney, Agent, or Firm—Merchant & Gould P.C.

(57) ABSTRACT

Tissue-equivalent and biopolymer tubes and rods include fibrils which are oriented (aligned) by a magnetic field. These oriented fibrils provide enhanced mechanical and cell guidance properties to the tissue-equivalent and biopolymer tubes. One such tissue-equivalent tube includes a body of collagen gel with mammalian tissue cells interspersed therein. The collagen fibrils are circumferentially oriented within the tubular body by a magnetic field, thereby inducing circumferential orientation of the cells. One such biopolymer rod includes collagen fibrils longitudinally oriented along the rod axis by a magnetic field that guides invasion of cells. Methods of making magnetically oriented tissue-equivalent and biopolymer tubes and rods are also disclosed.

9 Claims, 10 Drawing Sheets

OTHER PUBLICATIONS

Fung, Y. C., "5.14 The hypothesis of a solid–like cell content", from *Biomechanics—Mechanical Properties of Living Tissues*, Second Ed., Springer–Verlag New York, Inc. (1993); pp. 210–213.

Guenard et al., "Syngeneic Schwann Cells Derived from Adult Nerves Seeded in Semipermeable Guidance Channels Enhance Peripheral Nerve Regeneration", *The Journal of Neuroscience*, 12(9):3310–3320 (Sep., 1992).

Guido et al., "A Methodology for the Systematic and Quantative Study of Cell Contact Guidance in Oriented Collagen Gels. Correlation of Fibroblast Orientation and Gel Birefringence", *Journal of Cell Science*, 105:317–331 (1993).

Hirai et al., "Highly Oriented, Tubular Hybrid Vascular Tissue for a Low Pressure Circulatory System", *ASAIO Journal*, M383–M388 (1994).

Huang, D. et al., "Mechanisms and dynamics of mechanical strengthening in ligament–equivalent fibroblast–populated collagen matrices", *Annals of Biomedical Engineering*, 21(3):289–305 (May/Jun. 1993).

Ioku et al., "The Effect of Collagen Gel Matrix on Regeneration of Severed Rat Sciatic Nerve—Electromyographical and Morphological Study", *Electromyography and Clinical Neurophysiology*, 28 (7–8) 369–372 (Nov.–Dec. 1988).

Ives, C. L. et al., "Mechanical effects on endothelial cell morphology: In vitro assessment", *In Vitro Cellular & Developmental Biology*, 22(9):500–507 (Sep. 1986).

Jain, M. K. et al., "Mechanical stress and cellular metabolism in living soft tissue composites", *Biomaterials*, 11(7):465–472 (Sep. 1990).

Kanda et al., "Mechanical Stress Induced Cellular Orientation and Phenotypic Modulation of 3–D Cultured Smooth Muscle Cells", *ASAIO Journal*, M686–M690 (1993).

Kanda, K. et al., "In vitro reconstruction of hybrid vascular tissue", *ASAIO Journal*, 39(3):M561–M565 (Jul.–Sep. 1993).

Keeley et al., "Peripheral Nerve Regeneration Across 14–mm Gaps: A Comparison of Autograft and Entubulation Repair Methods in the Rat", *Journal of Reconstructive Microsurgery*, 9(5):349–358 (Sep., 1993).

Kim et al., Labeled Schwann Cell Transplants Versus Sural Nerve Grafts in Nerve Repair, *Journal of Neurosurgery*, 80(2):254–260 (Feb., 1994).

Kiyotani et al., "Experimental study of nerves regeneration in a biodegradable tube made from collagen and plyglycolic acid", *Asaio J.*, 41(3):M657–61 (1995).

Langer et al., "Tissue Engineering", *Science*, 260:920–926 (May 14, 1993).

Lefebvre, F. et al., "New artificial connective matrix–like structure made of elastin solubilized peptides and collagens: elaboration, biochemical and structural properties", *Biomaterials*, 13(1):28–33 (1992).

Liu, Z.–Q. et al., "Analysis directional features in images using gabor filters", *Third Annual IEEE Symnposium on Computer–Based Medical Systems*, pp. 68–74 (Jun. 1990).

Madison et al., "Point Sources of Schwann Cells Result in Growth into a Nerve Entubulation Repair Site in the Absence of Axons: Effects of Freeze–Thawing", *Experimental Neurology*, 128(2):266–275 (Aug., 1994).

Marchand et al., "Evaluation of Two Cross–Linked Collagen Gels Implanted in the Transected Spinal Cord", *Brain Research Bulletin*, 30:415–422 (1993).

Moon, A.G. et al., "Fibroblast–populated collagen microsphere assay of cell traction force: Part 1. Continuum Model", *AIChE Journal*, 39(1):163–177 (Jan. 1993).

Paino et al., "Regrowth of axons in lesioned adult rat spinal cord: promotion by implants of cultured Schwann cells", *J. Neurocytology*, 23(7):433–52 (1994).

Patterson et al., Design and Evaluation of a Sensory Feedback System that Provides Grasping Pressure in a Myoelectric Hand, *Journal of Rehabilitation Research and Development*, 29(1):1–8 (1992).

Rosen et al., "Artificial Nerve Graft Using Collagen as an Extracellular Matrix for Nerve Repair Compared with Sutured Autograft in a Rat Model", *Annals of Plastic Surgery*, 25(5):375–387 (Nov. 1990).

Sumpio, B. E. et al., "Response of porcine aortic smooth muscle cells to cyclic tensional deformation in culture", *Journal of Surgical Research*, 44:696–701 (1988).

Sumpio, B. et la., "Enhanced collagen production by smooth muscle cells during repetitive mechanical stretching", *Arch. Surg.* 123(10):1233–1236 (Oct. 1988).

Torbet et al., "Magnetic Alignment of Collagen During Self–Assembly", *Biochem Journal*, 219:1056–1059 (1984).

Torbet, "Fibrin Assembly in Human Plasma and Fibrinogen/Albumin Mixtures", *Biochemistry*, 25(18):4979–5350 (Sep. 9, 1986).

Tranquillo et al., 1996, *Biomaterials*, vol. 7, No. 3, pp. 349–357 "Magnetically Orientated Tissue–Equivalent Tubes: Application to a Circumferentially Orientated Media–Equivalent".

Utley et al., "Brain–Derived Neurotrophic Factor and Collagen Tubulization Enhance Functional Recovery After Peripheral Nerve Trransection and Repair", *Arch. Otolaryngol. Head Neck Surg.*, 122:407–413 (Apr. 1996).

Valentini et al., "Collagen–and Laminin–Containing Gels Impede Peripheral Nerve Regeneration through Semipermeable Nerve Guidance Channels", *Experimental Neurology*, 98:350–356 (1987).

Weinberg et al., "A Blood Vessel Model Constructed from Collagen and Cultured Vascular Cells", *Science*, 231:397–400 (Jan. 24, 1986).

Williams, 1987, *Neurochemical Research*, vol. 12, No. 10, pp. 851–860 "Exogenous Fibrin Matrix Precursors Stimulate the Temporal Progress of Nerve Regeneration Within a Silicon Chamber".

Wolinsky, H. et al., "Structural basis for the static mechanical properties of the aortic media", *Circulation Research*, 14:400–413 (Jan.–Jun. 1964).

Yannas et al., "Regeneration of Sciatic Nerve Across 15mm Gap by Use of a Polymeric Template," *Advances in Biomedical Polymers*, Plenum Press: 1–9 (©1987).

* cited by examiner

METHOD OF NERVE REGENERATION USING BIOPOLYMER RODS WITH ORIENTED FIBRILS

This application is a Continuation of application Ser. No. 08/725,916, filed Oct. 4, 1996 now U.S. Pat. No. 6,057,137, which is a Continuation-In-Part of application Ser. No. 08/703,928, filed Aug. 28, 1996 now U.S. Pat. No. 5,948, 654, Continuation of application Ser. No. 08/319,291, filed Oct. 6, 1994, now abandoned. These applications are incorporated herein by reference.

GOVERNMENT SUPPORT

This invention was made with Government support under Presidential Young Investigator Award BCS-8957736 and BES-9522758, awarded by the National Science Foundation. The Government has certain rights in the invention.

FIELD OF THE INVENTION

This invention relates to oriented tissue-equivalent and biopolymer tubes and in particular bioartificial arteries made of Type I collagen formed into tubes having collagen fibrils circumferentially oriented by a magnetic field. The present invention additionally relates to tissue regeneration structures, and in particular tissue-equivalent and biopolymer rods for nerve regeneration.

BACKGROUND OF THE INVENTION

The demand for artificial blood vessels, and in particular, artificial arteries is great. This is due to the fact that over 600,000 surgical procedures involving large and small blood vessels are conducted annually.

Arteries are complex structures, as the cellular and extracellular components of the artery wall are not uniformly distributed. Rather, these cellular and extracellular components are organized into discrete layers. These discrete layers have a trilaminant structure of an intima, a media and an adventitia.

The mechanical properties of the artery wall are largely due to components of the vessel media layer. Elastin is the most extensible component of the vessel media, whereas collagen is relatively stiff. The presence of smooth muscle cells is important for two reasons. First, the smooth muscle cells synthesize the elastin and collagen present in the vessel media and second, they are capable of contraction and relaxation in response to various external stimuli including vasoactive substances in the blood and sympathetic and parasympathetic nerve impulses. These smooth muscle cells are thus an important source of structural protein that contribute directly to the strength and elasticity of the vessel wall and represent a component of variable elasticity participating in the regulation of vessel tone.

The elastin and collagen components confer a non-linear stress-strain relationship, in which the elastic modulus of the vessel wall increases (the vessel becomes stiffer) as the vessel is distended. The importance of organization to mechanical function in the arterial wall is clearly seen when arteries are compared to veins of similar size. In arteries, the circumferentially or (helically) oriented smooth muscle cells and associated elastin and collagen of the media, provide the mechanical strength necessary to withstand the higher pressures that exist in the arterial circulation. In contrast, the media layer of a vein of similar size is reduced in thickness, contains fewer smooth muscle cells, less elastin, and lastly little circumferential orientation of smooth muscle collagen and elastin seen as in the arteries.

Several attempts have been made at creating a completely bioartificial artery. Weinberg and Bell, "A Blood Vessel Model Construction from Collagen and Cultured Vascular Cells" in *Science*, Vol. 231 (1986), pp. 397–400, reported production of an artery involving smooth muscle cells and fibroblasts in layers of reconstituted Type I collagen that approximate the laminate structure, but not the circumferential orientation of natural arteries. These vessel analogs lacked the mechanical strength necessary to withstand the stress associated with pulsatile blood flow in vivo. To increase the strength, proponents of the Weinberg and Bell approach were forced to reinforce these arteries with synthetic polymer sheaths, such as Dacron®. These bioartificial arteries exhibit a severe drawback in that biocompatability problems can ultimately lead to graft failure as reported by Langer and Vacanti, "Tissue Engineering" in *Science*, Vol. 260 (1993), pp. 920–926. Kanada et al., "Mechanical Stress Induced Cellular Orientation and Phenotypic Modulation of 3-D Cultured Smooth Muscle Cells" in *ASAIO Journal*, (1993), pp. M686–M690, reported a biohybrid vessel which includes polyurethane in order to obtain the appropriate mechanical properties.

The orientation of fibrils and cells in collagen has been studied. For example, Torbet and Ronziere, "Magnetic Alignment of Collagen During Self-Assembly" in *Biochem. J.*, Vol. 219 (1984), pp. 1057–1059, reported collagen fibril orientation in the presence of a magnetic field. Additionally, Guido and Tranquillo, "A Methodology for the Systematic and Quantitative Study of Cell Contact Guidance in Oriented Collagen Gels" in *Journal of Cell Science*, Vol. 105 (1993), pp. 317–331, reported that cells orient in the same direction as the oriented collagen fibrils, under the phenomen known as "cell contact guidance".

Despite the study of fibril and cell orientation, there remains the need to provide a tissue-equivalent tube that has mechanical properties that enable it-to better withstand distention, typically associated with pulsatile blood flow in arteries, without reinforcing synthetic materials.

Additionally, regeneration of severed peripheral nerves commonly results in permanent damage and disability because mature neurons do not normally replicate. Once severed, the severed ends of the neurons usually grow in a misdirected manner, such that they do not reestablish the original connection. Numerous attempts have been made to reestablish the connections, including the placement of a tube filled with a matrix for bridging the nerve endings. For Example, Rosen, "Artificial Nerve Graft Using Collagen as an Extracelluar Matrix for Nerve Repair Compared with Suture Autograft in a Rat Model", in *Annals of Plastic Surgery*, 25:375–387 (1990) reported slightly inferior nerve regeneration using tubes filled with collagen gel as compared to nerve autografts, whereas Valentini, et al., "Collagen and Laminin Containing Gels Impede Peripheral Nerve Regeneration through Semipermeable Nerve Guidance Channels", in *Experimental Neurology*, 98:350–356 (1987) reported greatly inferior nerve regeneration as compared to saline-filled tubes.

SUMMARY OF THE INVENTION

The present invention comprises a tissue-equivalent tube that has a cylindrical body made of a reconstituted collagen network with smooth muscle cells interspersed therein. The collagen network is comprised of fibrils that orient circumferentially within the tubular body. The cells are induced by the oriented fibrils to also orient circumferentially. The circumferential orientation of fibrils and cells is characteristic of a native artery and results in improved mechanical properties.

The tissue-equivalent tube is formed by a tubular mold having a central rod and a concentric outer member, aligned to provide a cavity between the central rod and the outer member. The mold includes a longitudinal axis, extending the length of the mold. The cavity is then filled with a solution of collagen and mammalian tissue cells. In one embodiment, the filled tubular mold is then placed into a high strength magnetic field such that the longitudinal axis of the tubular mold is substantially parallel to the direction of the magnetic field. The magnetic field orients the forming collagen fibrils normal to the direction of the magnetic field, such that the collagen fibrils are oriented circumferentially with respect to the tube.

The invention additionally comprises tissue-equivalent and biopolymer rods, along with methods for their manufacture and use. In particular, these tissue-equivalent and biopolymer rods include axially (longitudinally) aligned collagen fibrils that provide a guidance field to exploit the contact response in growth cones at the tips of severed nerve endings (neurite tips) to effectively direct nerve cell growth across the gap between severed nerve endings, regenerating mature nerves.

The tissue-equivalent rods are formed by using a cylindrical (rod-shaped) mold with a cavity therein, including a longitudinal axis extending the length of, the mold and a transverse axis extending the width of the mold. The cavity is then filled with a solution of collagen and mammalian tissue cells, preferably Schwann Cells. In one embodiment, the filled cylindrical mold is then placed into a high strength magnetic field such that the longitudinal axis of the tubular mold is substantially perpendicular to the direction of the magnetic field. The magnetic field aligns (orients) the forming collagen fibrils normal (perpendicular) to the direction of the magnetic field, such that the collagen fibrils are aligned (oriented) substantially parallel to the direction of the longitudinal axis.

The biopolymer rods are formed by using a cylindrical mold with a cavity therein, including a longitudinal axis extending the length of the mold and a transverse axis extending the width of the mold. The cavity is then filled with a solution of collagen and polymer beads, that include encapsulated neurotrophic factors. In one embodiment, the filled cylindrical mold is then placed into a high strength magnetic field such that the longitudinal axis of the cylindrical mold is substantially perpendicular to the direction of the magnetic field. The magnetic field aligns (orients) the forming collagen fibrils normal (perpendicular) to the direction of the magnetic field, such that the collagen fibrils are aligned (oriented) substantially parallel to the direction of the longitudinal axis.

BRIEF DESCRIPTION OF THE DRAWINGS

The present invention will be described with reference to the accompanying drawings, wherein like reference numerals identify like components.

In the drawings:

FIG. 11b is a perspective view of the axially aligned biopolymer or tissue-equivalent (collagen gel) rod of the present invention being applied to the severed nerve of FIG. 11a;

DETAILED DESCRIPTION OF THE INVENTION

As used in the present invention, "tissue-equivalent tubes" or "tissue-equivalent rods" refer to tubes or rods formed of collagen or fibrin and mammalian tissue cells. "Biopolymer tubes" or "biopolymer rods" refer to tubes or rods formed of collagen or fibrin, without the mammalian tissue cells. The term "oriented", refers to the fibrils of the collagen or fibrin, which form the tissue-equivalent or biopolymer tubes, or rods, respectively, being substantially aligned in a specific direction, e.g., axially (along the longitudinal axis of the tube or rod).

The oriented tissue-equivalent tubes of the invention are formed of a solution comprising collagen and mammalian tissue cells, placed into a tubular mold, and subjected to a magnetic field, causing the forming collagen fibrils to become oriented in a direction substantially normal to the direction of the magnetic field. Accordingly, a filled tubular mold placed into the magnetic field, such that its longitudinal axis is parallel to the magnetic field, will have circumferentially oriented fibers, while a filled tubular mold, placed into the magnetic field such that its longitudinal axis is substantially perpendicular to the direction of the magnetic field, will have axially oriented fibrils.

Additionally, biopolymer tubes can be made of pure collagen. Unlike the tissue-equivalent tubes, these biopolymer tubes lack mammalian tissue cells. However, similar to the tissue-equivalent tubes made of the collagen solution (collagen and mammalian tissue cells), the collagen fibrils orient in the desired direction based upon the positioning of the filled tubular mold with respect to the direction of the magnetic field.

Moreover, tissue-equivalent tubes and biopolymer tubes could be made by the method of the present invention by another tissue matrix material such as fibrin. A fibrin-forming solution, prepared in accordance with conventional methods known in the art, would be placed in a tubular mold and subjected to a magnetic field. As reported by Torbet, "Fibrin Assembly in Human Plasma and Fibrinogen/Albumin Mixtures" in *Biochemistry*, Vol. 25 (1986), pp. 5309–5314, which is incorporated by reference herein, fibrin fibrils, when subjected to a magnetic field, orient in a direction substantially parallel to the direction of the magnetic field. This behavior in the presence of a magnetic field is opposite that of collagen fibrils. Accordingly, a tubular mold formed with fibrin-forming solution, and placed into the magnetic field such that its longitudinal axis is parallel to the magnetic field will have axially oriented fibers, while a filled tubular mold placed into the magnetic field such that its longitudinal axis is substantially perpendicular to the direction of the magnetic field will have circumferentially oriented fibrils.

The collagen referred to above is any monomeric collagen, that self-assembles into fibrils, such as Type I collagen or the like, prepared by any conventional procedures. The mammalian tissue cells referred to above could be grown by any conventional cell growth and culturing method. The tubular molds referred to above could be any mold having a solid rod concentric with an outer member. Both the solid central rod and the outer member are made of materials which will not adhere to the gelled solution, in order that a tube with an open central lumen can be removed.

The present invention envisions molds of single and multiple piece construction. For example, the solid central rod and outer member can be discrete members. In such a case, the outer member is preferably a cylindrical tube. However, rectangular or hexagonal shaped tubes, or the like may also be used. A separate solid rod serves as a second component of the mold. This rod can be formed as a separate member, attached to a plunger (if a syringe barrel forms the outer member) or other portion of the outer member of the mold. The solid rod can also be formed integral with the plunger. Alternately, a single piece construction, having a formed outer member, bore, barrel, or the like, with an internally positioned axial rod component is permissible. The dimensions and spatial relationships of the outer member and central rod can be varied by one skilled in the art, based on the disclosures herein. Additionally, the tubular mold, or various components thereof, can be made of materials such as Teflon® polyethylene, polypropylene, polyurethane, other equivalent plastic materials, or other non-porous non-magnetic materials.

Figure 1:
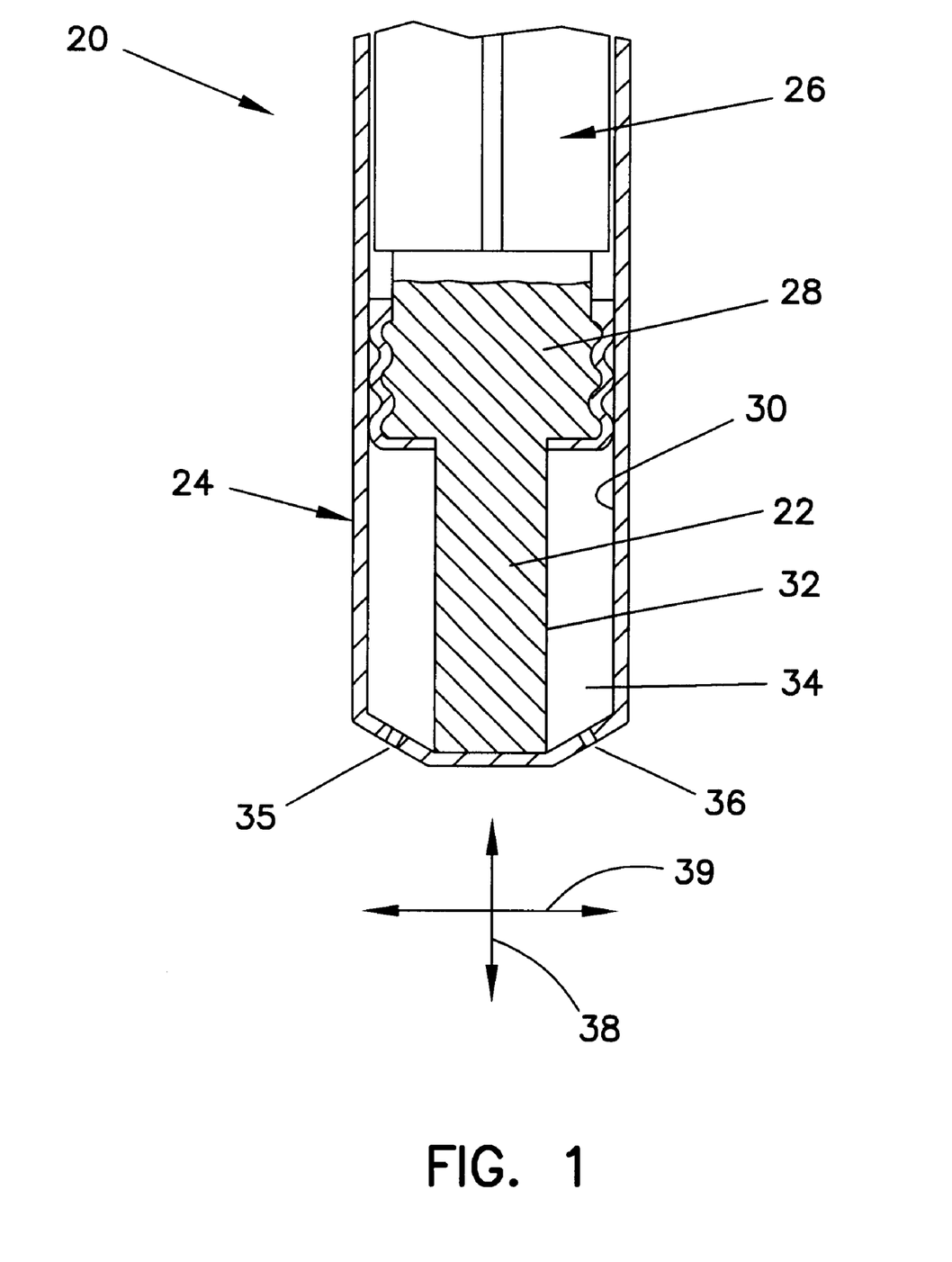
FIG. 1 is a side view of the tubular mold of the present invention.

Turning now to the drawing figures, which show embodiments of the present invention, FIG. 1 shows a tubular mold 20 for making the tissue-equivalent tubes and biopolymer tubes of the invention. The tubular mold 20 is formed from a Teflon® rod 22 and a cylinder 24, preferably formed of a syringe barrel. The Teflon® rod 22 is attached to a plunger 26 at the plunger disc 28. The disc 28 frictionally engages the inner surface 30 of the cylinder 24.

The Teflon® rod 22 is preferably at the center of the cylinder 24. The inner surface 30 of the cylinder 24 and the outer surface 32 of the Teflon® rod 22 are spaced apart such that there is a tubular cavity 34 in the space therebetween. The Teflon® rod 22 is positioned in this manner to provide the resultant tubes 40, 50, 60 (FIGS. 2–4) with a central lumen 44, 54, 64 (FIGS. 2–4) upon removal from the tubular mold 20. The tubular mold 20 includes an opening 35 for receiving the collagen solution and openings 36 for releasing air displaced by the collagen solution. The tubular mold 20 is designed such that a collagen solution injected therein can be easily removed as a collagen tube.

This tubular mold 20 includes a longitudinal axis 38 and a transverse axis 39. These axes 38, 39 will be used to illustrate the directions of fibril orientation.

Figure 2:
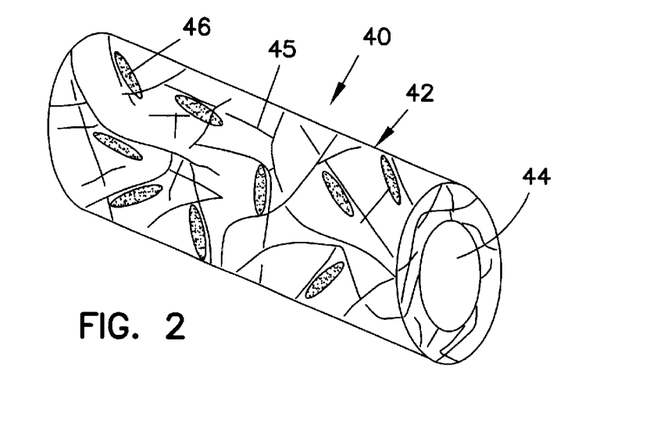
FIG. 2 is an illustration of a control tissue-equivalent tube.

FIG. 2 shows a tissue-equivalent tube 40, made from the tubular mold 20 of FIG. 1, that is used as a control. The tube 40 has a cylindrical body 42 around a central lumen 44. The body 42 includes randomly oriented collagen fibrils 45 and mammalian tissue cells 46. The tube 40 is formed from a solution of collagen and mammalian tissue cells injected into the tubular mold 20 (FIG. 1) and removed once the collagen has self-assembled into fibrils 45 entrapping the mammalian tissue cells 46.

The collagen used for this control tube 40 is preferably monomeric Type I collagen, or the like, in a cold (approximately 5° C.) neutral solution. The mammalian tissue cells are preferably smooth muscle cells having been grown by conventional cell growth and culture methods, well known to those skilled in the art. The mammalian tissue cells are then dispersed into the cold collagen solution in accordance with the procedure detailed below in Example 1.

The cold solution is then injected into small (pinhole sized) openings 35 in the tubular mold 20. Fibrillogenesis begins as the tubular mold 20 (FIG. 1) is then transferred to a constant temperature box, for incubation in the temperature range of approximately 30° C. to 40° C. for approximately two hours, during which firbillogenesis is normally completed. These steps, as well as additional steps required to complete the fabrication of the control tube 40, are described in detail in Example 1, below.

Figure 3:
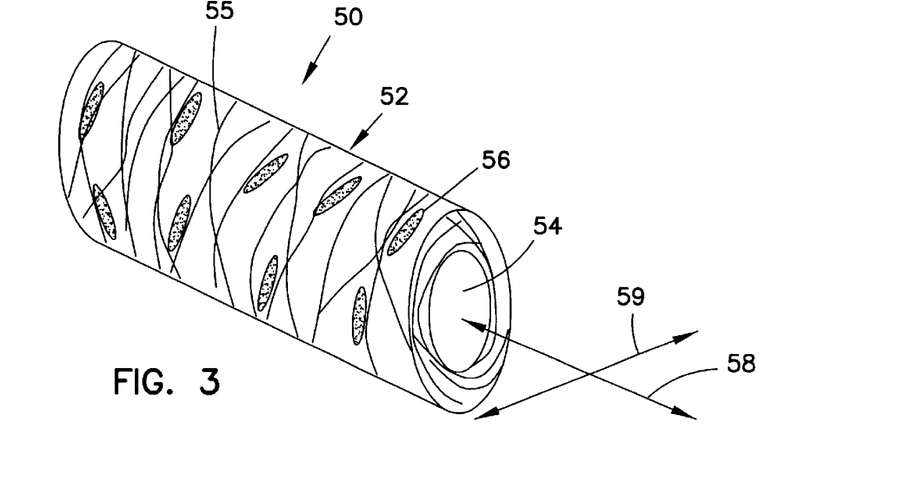
FIG. 3 is an illustration of a circumferentially oriented tissue-equivalent tube of the present invention.

FIG. 3 shows a tissue-equivalent tube 50 of the invention. This tube 50 has a cylindrical body 52 around a central lumen 54. The body 52 includes circumferentially oriented collagen fibrils 55 and mammalian tissue cells 56. The tube 50 includes a longitudinal axis 58 and a transverse axis 59 and is formed from a solution of collagen, including fibrils 55, with mammalian tissue cells 56. The collagen fibrils 55 and mammalian tissue cells 56 of this tube 50 are circumferentially oriented along the transverse axis 59. This circumferential orientation of fibrils 55 and mammalian tissue cells 56 in the tube 50 provides enhanced mechanical strength in the transverse direction, to help prevent it from longitudinal splitting. Additionally, it is believed that the mammalian tissue cells 56, further mechanically strengthen the circumferentially oriented tube 50 by a phenomenon known as "cell traction". This phenomenon of "cell traction" occurs as the mammalian tissue cells 56 place the fibrils 55 in tension while elaborating other reinforcing extracellular matrix molecules, such as elastin, in the collagen, as they differentiate in the tissue-equivalent environment.

The collagen used for the tube 50 of the invention is identical to that described above in reference to the control tube 40 of FIG. 1. The mammalian tissue cells 56 are preferably smooth muscle cells, identical to those described above in reference to the control tube 40 of FIG. 1.

The solution of collagen and mammalian tissue cells is prepared as described for the control tube 40 of FIG. 1, above (as described in detail in Example 1, below), except that the initiation of fibrillogenesis is substantially simultaneous with the filled tubular mold 20 (FIG. 1) being placed into a high strength (4.7 to 9 Tesla) magnetic field. The magnetic field is preferably a static magnetic field generated by a horizontal bore electromagnet, such as a 4.7 Tesla Model, from the Oxford Company of the United Kingdom. Specifically, the filled tubular mold 20 (FIG. 1) is placed into the magnetic field at an orientation such that its longitudinal axis 38 (FIG. 1) is parallel to the direction of the magnetic field. This incubation, where collagen fibril orientation occurs lasts approximately two hours. These steps are described in detail in Example 2, below.

This positioning of the filled tubular mold 20 (FIG. 1) in the magnetic field causes the growing collagen fibrils 56 to orient circumferentially in the direction of the transverse axis 39 (FIG. 1). The orientation of the fibrils 55 is additionally aided by alteration of the parameters, one parameter being the distance between the outer surface of the Teflon® rod 32 (FIG. 1) and the inner surface of the outer cylinder 30 (FIG. 1). By having a cavity 34 (FIG. 1) with a short distance between the surfaces 30, 32, the orienting effect of the magnetic field in the growing fibrils in the circumferential direction is maximized as the surfaces of the Teflon® rod 22 and the cylinder 24 (FIG. 1) assist in the alignment.

In the present invention, the smooth muscle cells are induced to exhibit circumferential orientation (induced by the circumferentially oriented fibrils described above), similar to that of the smooth muscle cells in the medial layer of an artery. According to the method described herein, this smooth muscle cell orientation contributes to the mechanical properties of the circumferentially oriented tube 50.

The circumferentially oriented tissue-equivalent tubes of the invention are useful as artificial blood vessels, and in particular arteries, as they are reinforced in a circumferential direction, providing additional strength to withstand the distension associated with pulsatile blood flow. However, these oriented tissue-equivalent tubes, along with tissue-equivalent tubes having fibrils aligned along the longitudinal axis 58 of the tube, known as "axially oriented" (produced by the method detailed in Example 2, below, except that the fibril orienting step is such that the filled mold is placed such that its longitudinal axis is substantially perpendicular to the direction of the magnetic field, during fibrillogenesis), may find use as bioartifical ureters, urethras, tracheas, an esophagus, intestines, and other tubular organs. Sheets of this material could also be produced using sheet molds instead of the tubular molds described above, in order to produce planar structures such as skin or bladders.

Alternately, the cold collagen solution may be kept pure (i.e., without cells) and formed into oriented biopolymer tubes in accordance with the procedures detailed below in Examples 1 and 2. If an axially oriented biopolymer tube formed from this pure cold collagen solution were desired, the orientation step (detailed in Example 2, below), would be such that the filled tubular mold would be placed into the magnetic field such that its longitudinal axis is substantially perpendicular to the direction of the magnetic field. With respect to these tubes, they would be weaker than those with the smooth muscle cells, for the smooth muscles cells enhance the mechanical properties of the tubes.

Figure 4:
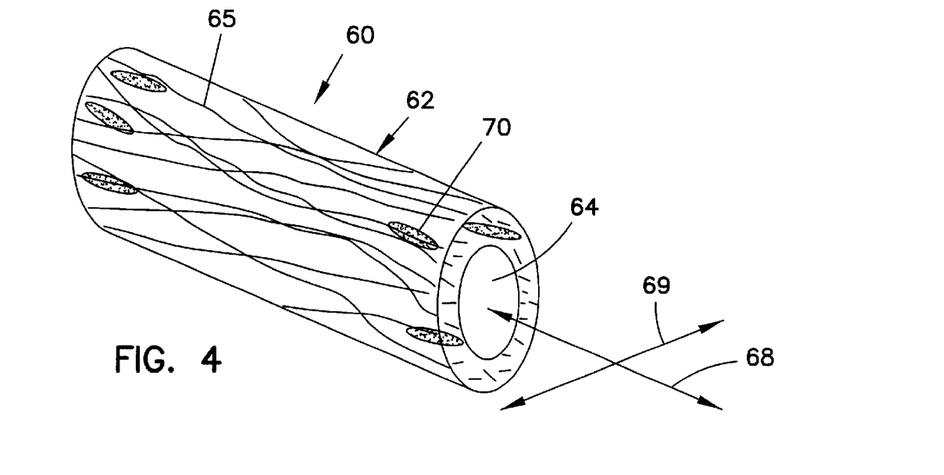
FIG. 4 is an illustration of an axially oriented biopolymer tube of the present invention.

FIG. 4 shows a biopolymer tube 60 of the invention. This tube 60 has a cylindrical body 62 around a central lumen 64. The body 62 includes fibrin fibrils 65 oriented along the longitudinal axis 68, known as "axially oriented". The tube 60 also has a transverse axis 69. The tube 60 is formed from a fibrin-forming solution including fibrinogen and thrombin, prepared in accordance with that described in Torbet, "Fibrin Assembly in Human Plasma and Fibrinogen/Albumin Mixtures" in *Biochemistry*, Vol. 25 (1986), pp. 5309–5314. This fibrin-forming solution is then made into an axially oriented biopolymer tube in accordance with Examples 1 and 2 below. However, should a tissue-equivalent tube with circumferentially oriented fibrin fibrils (oriented along the transverse axis 69) be desired, the orientation step would be opposite that disclosed in Example 2 below, as the filled tubular mold 20 (FIG. 1) would be placed into the magnetic field such that its longitudinal axis 68 is perpendicular to the direction of the magnetic field.

These axially oriented fibrin tubes, as well as axially oriented collagen biopolymer tubes (discussed above) are particularly useful as nerve regeneration conduits. This is due to the fact that the axially oriented fibrils 65 can serve to guide the inward growth and movement of host neurons 70 at opposite ends of the tube 60, such that the neurons at each end ultimately grow together. Rejoining of the severed nerve would occur in less time as compared to a randomly oriented biopolymer tube.

Figure 5:
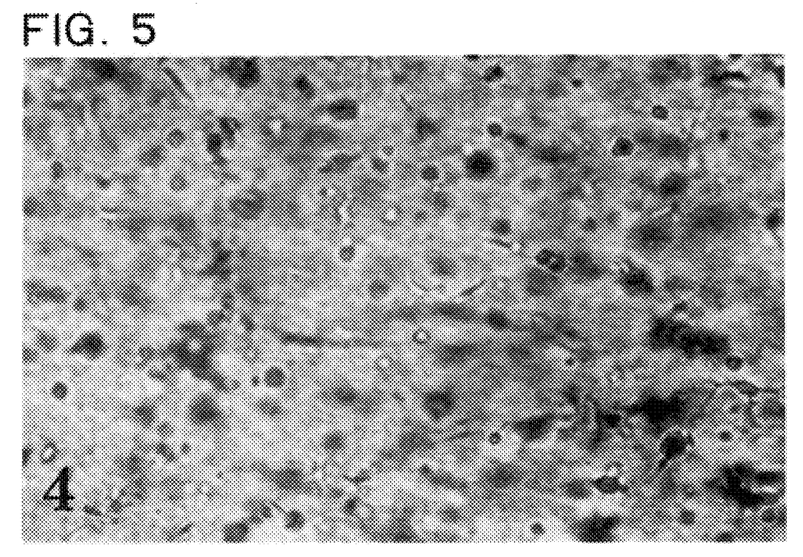
FIG. 5 is a micrograph of the control tissue-equivalent tube.
Figure 6:
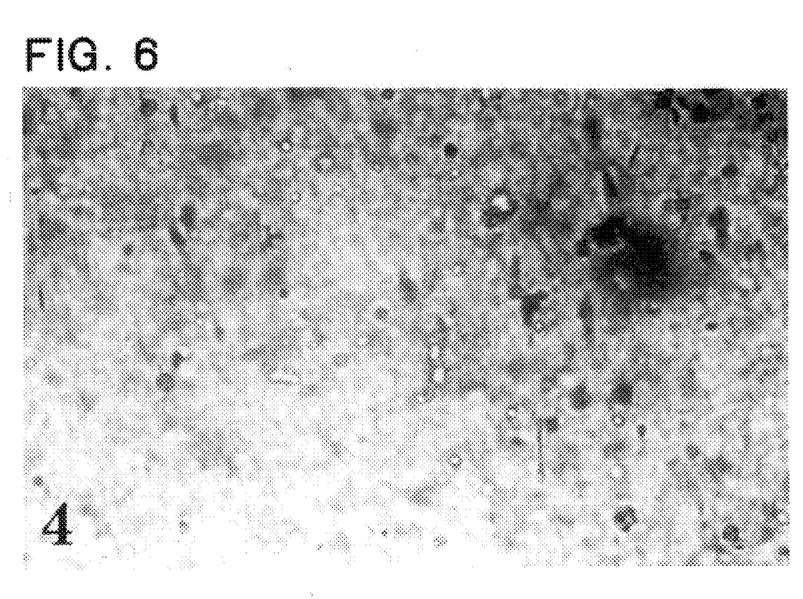
FIG. 6 is a micrograph of the circumferentially oriented tissue-equivalent tube of the present invention.

Turning now to FIGS. 5 and 6, there are shown micrographs of a control tissue-equivalent tube (FIG. 5) and a circumferentially oriented tissue-equivalent tube (FIG. 6), produced in accordance with the invention, as detailed in Examples 1 and 2 below. In FIGS. 5 and 6, the horizontal dimension is coincident with the longitudinal direction of the tube and the vertical dimension is coincident with the circumferential (transverse) direction of the tube. In FIG. 5, the cells appear randomly oriented in this control tube, while in FIG. 6, the cells appear circumferentially oriented.

Figure 8:
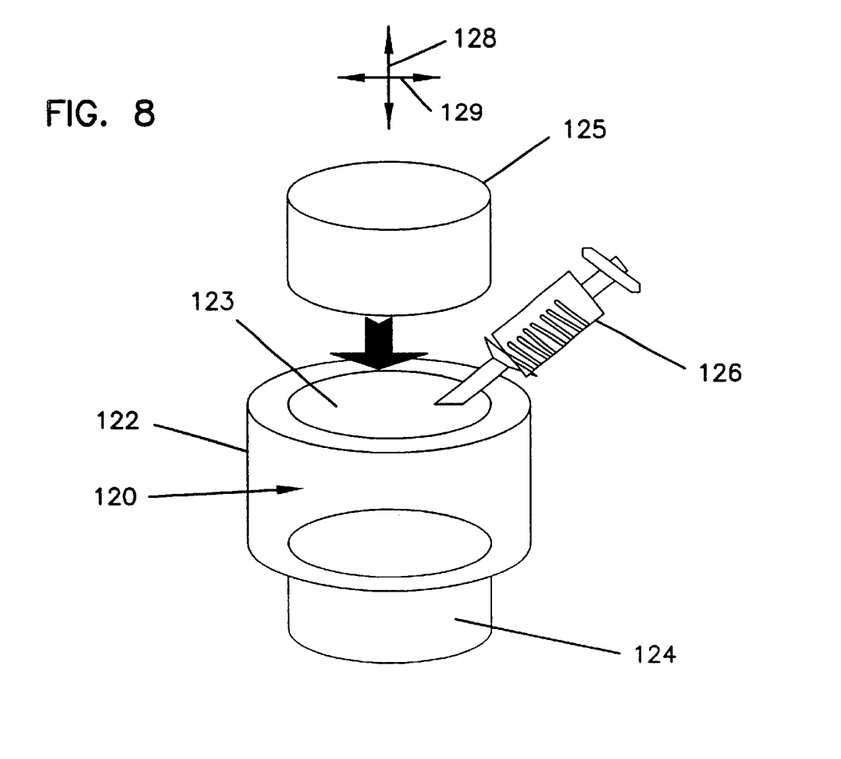
FIG. 8 is a perspective view of a cylindrical mold of the invention.
Figure 9:
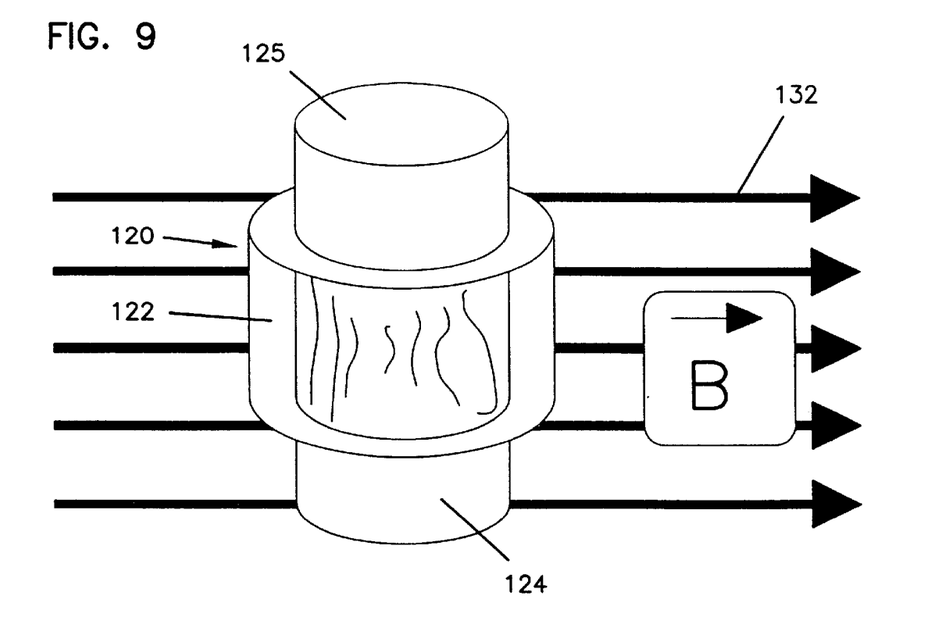
FIG. 9 is a perspective view of the cylindrical mold of the invention having been filled with a collagen solution that is forming collagen fibrils in the presence of a magnetic field (B)

Turning now to FIGS. 8 and 9, there is shown a cylindrical mold 120 for making the tissue-equivalent and biopolymer rods 130 (FIG. 10) of the present invention. These tissue-equivalent and biopolymer rods 130 are manufactured similarly, with the differences in the manufacturing steps noted below.

Figure 10:
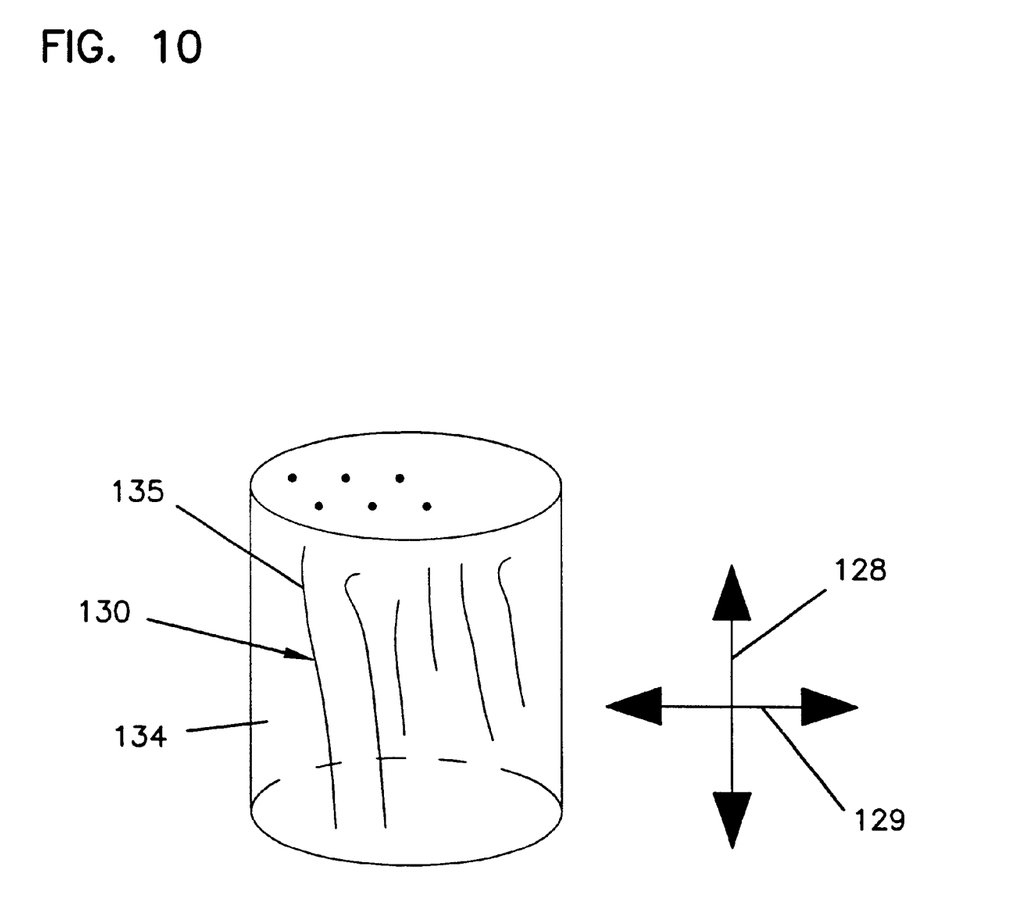
FIG. 10 is a perspective view of an axially aligned biopolymer or tissue-equivalent (collagen gel) rod of the present invention.

The cylindrical mold 120 for making these tissue-equivalent and biopolymer rods 130 is preferably formed of a TEFLON® cylinder 122 (preferably approximately 15 mm in length) having a cavity (lumen) 123, preferably of a diameter corresponding to that of a peripheral nerve (approximately 0.5–2 mm). The ends of the cylinder 122 receive plugs 124, 125. Alternately, biodegradable or bioresorbable polymer cylinders may be used as the cylindrical mold 120.

A first plug 124 is initially pushed into the cylinder 122 for the mold to receive collagen solution (made in accordance with the solutions described herein), preferably by injection from a syringe 126. Once the cavity (lumen) 123 is filled, the second plug 125 is fitted into the cylinder 122 The cylindrical mold 120 is designed such that the collagen solution injected therein can be easily removed as a collagen gel rod. Alternately, if the biodegradable or bioresorbable cylinder is used as the cylindrical mold, the collagen gel rod is not removed from the biodegradable or bioresorbable cylinder.

This cylindrical mold 120 includes a longitudinal axis 128 and a transverse axis 129. These axes 128, 129 will be used to illustrate the directions of fibril alignment (orientation) in the resultant tissue-equivalent and biopolymer rods.

The collagen used for these tissue-equivalent or biopolymer rods is preferably monomeric Type I collagen, or the like, in a cold (approximately 5° C.) neutral solution, prepared in accordance with Example 1 below. If a tissue-equivalent rod is desired, the solution includes mammalian tissue cells, that are preferably Schwann Cells and/or fiboblasts/endothelial cells, having been grown by conventional cell growth and culture methods, well known to those skilled in the art. The mammalian tissue cells are then dispersed into the cold collagen solution in accordance with the procedure detailed below in Example 1, except that the smooth muscle cells (mammalian tissue cells of Example 1) are substituted with Schwann Cells and/or fiboblasts/endothelial cells.

Alternately, if a biopolymer rod is desired, in a preferred step, small (approximately 10–15 micrometer diameter) biodegradable/bioresorbable polymer beads with encapsulated neurotrophic factors (such as nerve growth factor) are added to the cold collagen neutral solution. These biodegradable/bioresorbable polymer beads would be added to the collagen solution similar to the mammalian tissue cells, in accordance with Example 1 below. The polymer beads would function similar to the Schwann cells, of the tissue-equivalent rods, by releasing the encapsulated neurotropic factor(s) that serve as an additional stimulus for neural growth (e.g., neurite elongation).

The cold solution is then injected from the syringe 126 into the cavity 123 of the cylindrical mold 120. Injection of the solution is preferably done slowly to-avoid formation of air bubbles or air pockets. In accordance with Example 2, as detailed below, fibrillogenesis begins as the filled cylindrical mold 120 (FIG. 9) is then transferred to a constant temperature box, for incubation in the temperature range of approximately 30° C. to 400° C., and is placed in a high strength (preferably at least 4 Tesla) magnetic field, as described above and in Examples 1 and 2 below, with the longitudinal axis 128 oriented substantially perpendicular to the direction of the magnetic field (B) (indicated by arrows 132), for approximately two hours. Additional detail for performing these steps is provided in Examples 1 and 2 below, except that the tissue-equivalent and biopolymer rods of the invention are subject to fibrillogenesis (collagen fibril self assembly) in the presence of a magnetic field.

Upon removal from the magnetic field, the now-formed tissue-equivalent and biopolymer rods are removed from the TEFLON® cylindrical molds, by allowing the rods to slide out of the molds. If the molds are formed of biodegradable or bioresorbable polymer cylinders, these cylinders are preferably not removed, and remain as part of the rod for subsequent use. The resultant rods may be subject to further processing by steps similar to those described in Example 2 below.

FIG. 10 shows a tissue-equivalent or biopolymer rod 130, made from the cylindrical mold 120. (The mammalian tissue cells of the tissue-equivalent rod and the polymer beads of the biopolymer rod are too small to be observed in this drawing figure.) The tissue-equivalent or biopolymer rod 130 preferably includes a cylindrical body 134 with longitudinally aligned (oriented) collagen fibrils 135, in the direction of the longitudinal axis 128. (In this drawing figure, the cylindrical mold 120, if a TEFLON® cylinder, has been removed.)

Figure 11A:
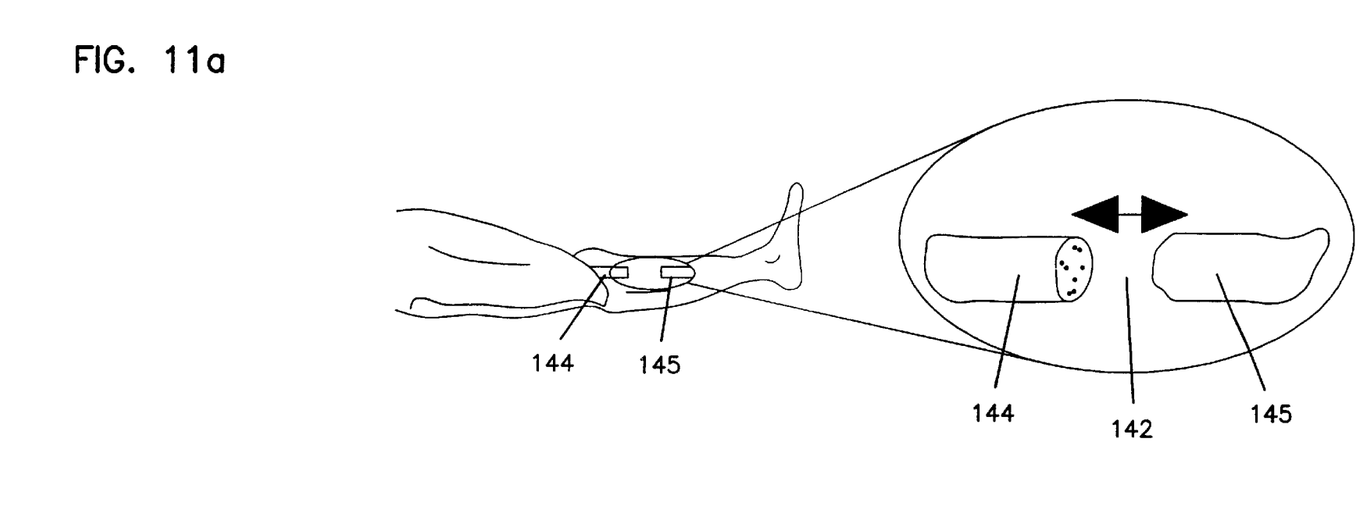
FIG. 11a is a perspective view of a severed nerve.
Figure 11B:
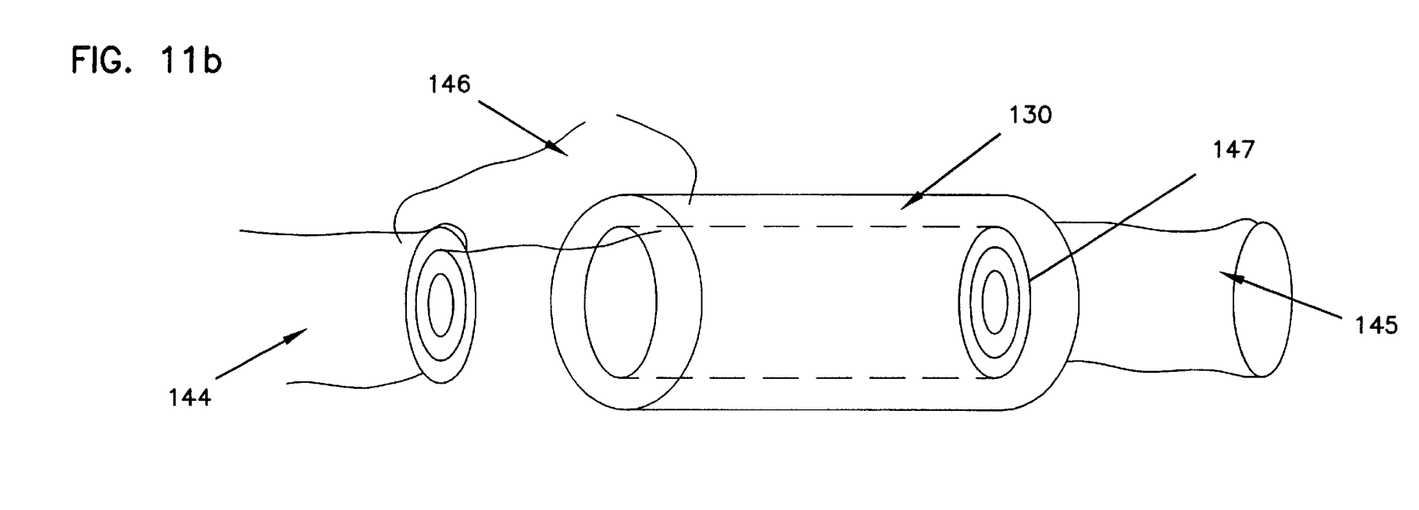

As stated above, one use of the tissue-equivalent rods and biopolymer rods 130 of the invention is for peripheral nerve regeneration. As shown in FIGS. 11a and 11b, there is a severed nerve 140 having a gap 142 between its severed ends 144, 145. The tissue-equivalent or biopolymer rod 130 is placed in the gap 142, and connected to each of the severed nerve ends 144, 145, for example, by sutures 146, 147. The tissue-equivalent or biopolymer rod 130 comprised of longitudinally aligned (oriented) collagen fibrils serves to guide neural growth across the gap between the severed nerve endings, thereby promoting regeneration of the original neural connection. This process has been simulated with a Dorsal Root Ganglia (DRG) from a chick embryo, and is detailed below in Examples 4–6.

Tissue-equivalent rods and biopolymer rods of fibrin may also be made in accordance with the invention. These tissue-equivalent and biopolymer rods have a cylindrical body, that includes fibrin fibrils oriented along the longitudinal axis (the longitudinal axis defined in accordance with FIGS. 8–10 above), known as "axially oriented". The rods is formed from a fibrin-forming solution including fibrinogen and thrombin, prepared in accordance with that described in Torbet, "Fibrin Assembly in Human Plasma and Fibrinogen/Albumin Mixtures" in *Biochemistry*, Vol. 25 (1986), pp. 5309–5314. In the case of tissue-equivalent fibrin rods, mammalian tissue cells (i.e., Schwann Cells and/or fibroblasts/endothelial cells) may be added to the fibrin-forming solution in accordance with the preparations discussed above. In the case of biopolymer fibrin rods, polymer beads (as discussed above), may be added to the fibrin-forming solution in accordance with the preparations discussed above. These fibrin-forming solutions are then placed into a cylindrical mold (of a TEFLON® cylinder, or a bioresorbable or biodegradable material cylinder) and made into an axially oriented biopolymer rod (with the resultant fibrils aligned in the direction of the longitudinal axis) in accordance with Examples 1 and 2 below (such that the cylindrical molds are placed into the magnetic field parallel to the direction of the magnetic field).

EXAMPLE 1

The control tube of FIG. 5 is prepared as follows. 20 microliters of cold (5° C.) HEPES Buffer Solution (1M) (No. 4573, *The Merk Index*, 11th ed.) are mixed with 50 microliters 10× Gibco Minimum Essential Medium (MEM) (Gibco BRL, Gaithersburg, Md. 20877) in a disposable 15 ml sterile vial. 132 microliters of room temperature NaOH (0.1N) is then added to the HEPES-MEM solution.

A solution is then prepared as 60 microliters of Fetal Bovine Serum (FBS) from Hyclone Laboratories, Inc., Logan, Utah 84321, 1 microliter of Penicillin-Streptomycin solution (5000 units of Penicillin and 5000 micrograms Streptomycin per millimeter in 0.85% saline solution) (Pen-Strep), and 10 microliters L-Glutamate solution (29.2 milligrams per milliliter) in 0.85% saline solution) are obtained from separate stocks, and each is frozen −20° C. The separate FBS, Pen-Strep, and L-Glutamate are warmed to room temperature and individually added to the 15 ml vial.

677 microliters of cold (5° C.) Vitrogen® 100 Collagen, available from Celtrix Pharmaceuticals, Inc., 3055 Patrick Henry Drive, Santa Clara, Calif. 95054, are then added and the solution is gently mixed with a pipette.

A cold (5° C.) cell suspension of smooth muscle cells (approximately $4 \times 10^6$ cells/ml) suspended in 50 microliters Gibco Medium 199 (M-199) (Gibco BRL, Gatithersburg, Md. 20877) is prepared. The solution includes rat aortic smooth muscle cells prepared in accordance with the method disclosed in Diglio, et al., "Rat Cerebral Microvascular Smooth Muscle Cells in Culture" in *J. Cell. Physiol.*, Vol. 129(2) (1986), pp. 131–141, which is incorporated by reference herein. The cells were maintained in Gibco Dulbecco's Modified Eagle Medium (DMEM) (Gibco BRL, Gaithersburg, Md. 20877) containing 10% Fetal Bovine Serum (FBS) and were subcultured twice weekly. Only cells below passage 25 that retain the phenotypic traits of expressing smooth muscle cell specific alpha-actin and myosin, and not the Factor VIII-related antigen were used here. This cold cell suspension is now added to the 15 ml vial.

The contents of the 15 ml vial are gently mixed with a pipette. The solution is kept on ice all the while. The cell and collagen solution is syringed out using standard sterile 3 milliliter syringes and is injected into a sterile mold. The mold was previously sterilized by soaking in 70% ethanol and followed by repeated rinsing with sterile water. The opening on the mold to inject the solution is covered with Parafilm® (American National Can Company, Chicago, Ill.) and the mold is placed on ice. The mold has an outer diameter of 1.2 centimeters and an inner diameter (for the central solid rod) of 0.635 centimeters, and a length of 1.2 centimeters. The process is repeated until the desired amount of molds are full. The molds are then placed in an incubator at 32° C. for two hours (the fibrillogenesis period).

EXAMPLE 2

The tubes of FIG. 6 were initially prepared in accordance with Example 1 above, except that the mold(s) once full are not placed in an incubator at 32° C. for the two hour fibrillogenesis period. Rather, the air and water tight molds are taken to a 4.7 Tesla magnet (Oxford Company, United Kingdom) on ice, and once there they are removed from the ice bath and placed in 1.25 inch thick styrofoam boxes filled with water at 32° C. The molds-are submerged in the water. The styrofoam box, containing the submerged molds, is then placed in a plastic bag and slid into the bore of the magnet, where the collagen solution in the molds is left to self-assemble for 2 hours (the fibrillogenesis period). In order to minimize gravity-induced cell settling during fibrillogenesis, the molds are briefly removed from the magnet and carefully rotated 180° and returned to the magnet. This procedure is done at 10 minute intervals.

When the two hours are up, the molds are removed from the magnet. Immediately, in a sterile hood, the molds are opened and the tissue-equivalent tubes are removed and placed in sterile 30 milliliter glass vials filled with 20 milliliters of M-199 cell culture medium supplemented with 5W (b y volume) L-Glutamine, Glutamine 5% (by volume) Fungizone® (E. R. Squibb & Sons, Inc., New York, N.Y.) (250 micrograms amphotericin B and 205 micrograms sodium deoxytcholate/milliliter in sterile/distilled water), 5% (by volume) Penicillin-Streptomycin solution (5000 units of Penicillin and 5000 micrograms steptomycin per milliliter in 0.85% saline solution), and 10% (by volume) Hyclone Fetal Bovine Serum. Smaller (⅛ inch) diameter sterile Teflon® rods are placed in the lumens of the tubes and they are subsequently placed in an incubator at 37° C. for extended periods of time (as long as is desired). The M-199 cell culture medium with supplements (described above) in the 30 ml glass vials is replaced at two day intervals.

EXAMPLE 3

Figure 7:
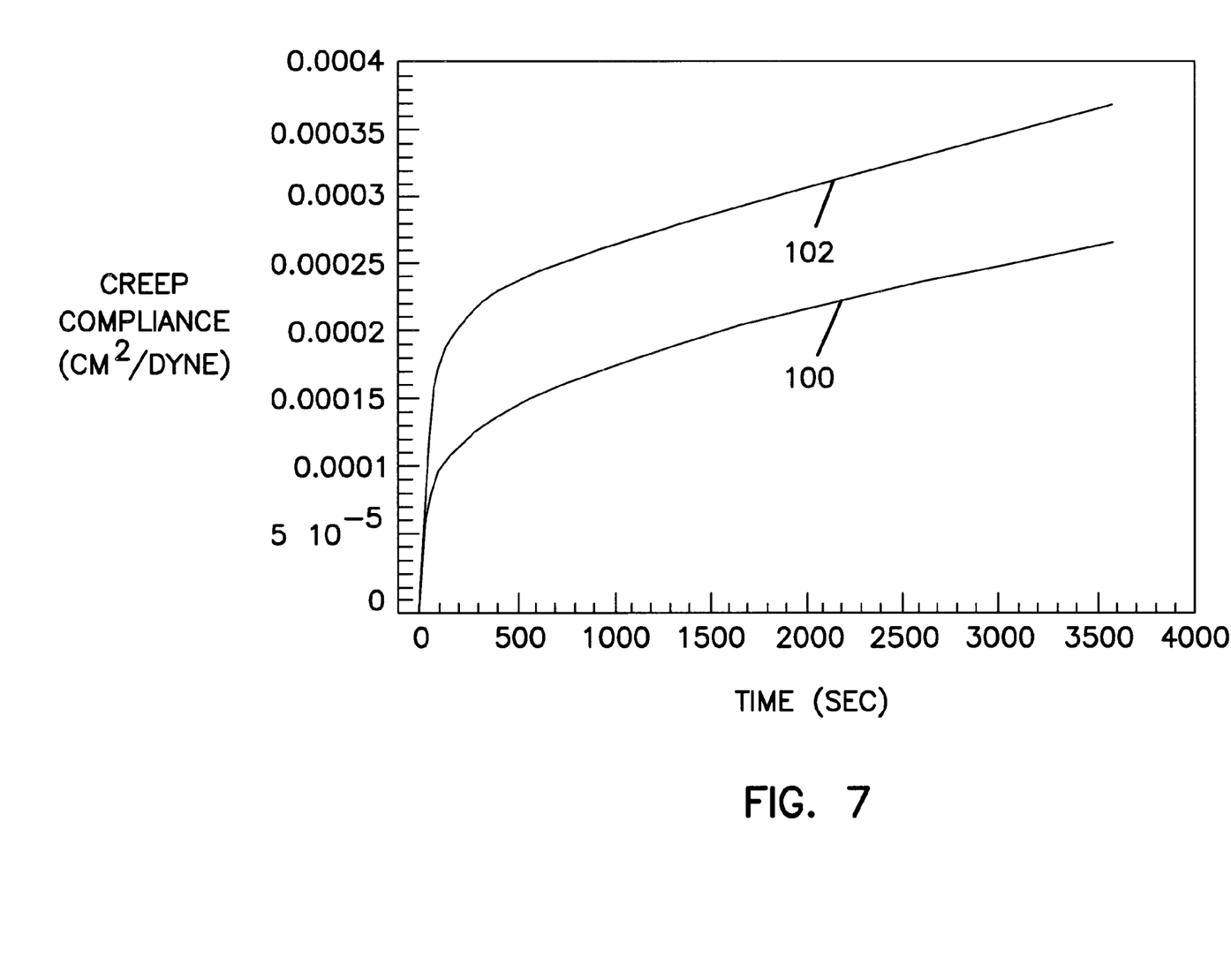
FIG. 7 is a chart of a creep test in the circumferential direction on the control tissue-equivalent tube and the circumferentially oriented tissue-equivalent tube of the present invention.

The control tissue-equivalent tube (FIG. 5) and the circumferentially oriented tissue-equivalent tube (FIG. 6) we re both subsequently cultured in an incubator at 37° C. for 108 hours and then tested on a Liveco Vitrodyne® 200, available from Liveco, Inc. of Burlington, Vt. The testing procedure involved first, slowly extending the tubes to a collapsed state and then allowing the tubes time to equilibrate before testing. This testing mode simulated distension in an artery. Creep compliance was measured over time and the results are plotted in FIG. 7. The circumferentially oriented tissue-equivalent tube response is line 100 while the unoriented (control) tissue-equivalent tube response is line 102. Based on these responses, the circumferentially oriented tube showed less instantaneous creep, as it was stiffer (less elastic) than the unoriented (control) tube. The creep rate at longer times is also somewhat less for the oriented tube (FIG. 6), indicating that it is also more viscous.

EXAMPLE 4

Figure 12A:
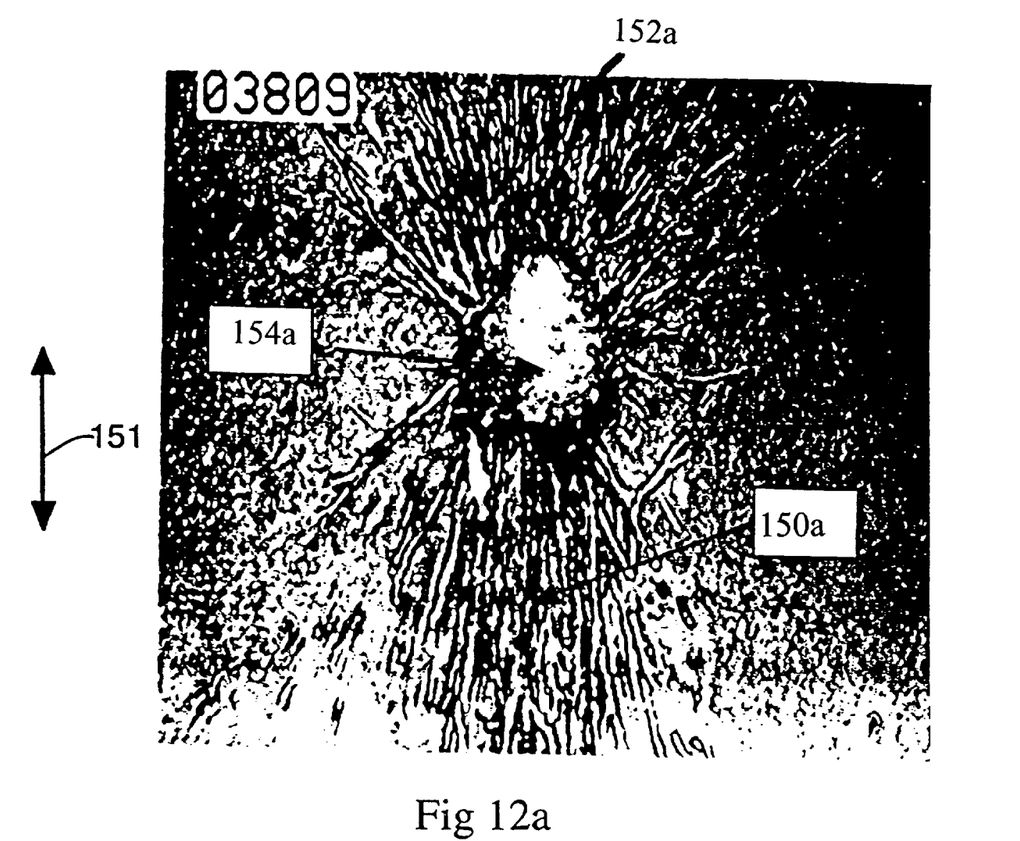
FIG. 12a is a micrograph of a dorsal root ganglia (DRG) cultured in an aligned biopolymer (collagen gel) rod.

Dorsal Root Ganglia (DRG) was explanted from a day 12 chick embryo and cultured (by direct entrapment) into an aligned biopolymer (collagen gel) rod, prepared in accordance with the above described methods for producing biopolymer rods of the present invention, except polymer beads (as described above) were not included. As illustrated in the micrograph of FIG. 12a, taken two days after the culture, the aligned biopolymer collagen gel rod 150a (having fibrils aligned in the direction of the arrow 151) showed neurites 152a that elongated from the DRG 154a in the same direction as the fibril alignment (orientation). The neurites were imaged by antibody staining (anti-neurofilment 200 KD).

EXAMPLE 5

Figure 12B:
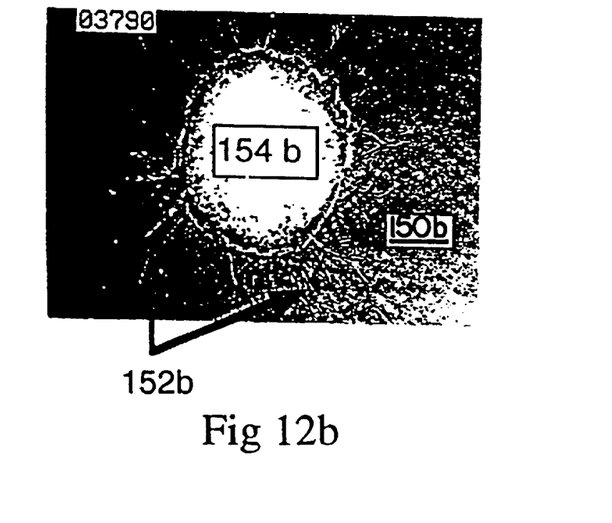
FIG. 12b is a micrograph of a dorsal root ganglia cultured in an isotropic biopolymer (collagen gel) rod.

Dorsal Root Ganglia (DRG) was explanted and cultured by direct entrapment from a day 12 chick embryo into an isotropic (non-aligned fibril) biopolymer (collagen gel) rod. The isotropic biopolymer (collagen gel) rod was prepared by the method described in Example 1. As illustrated by the micrograph of FIG. 12b, taken two days after the culture, the isotropic biopolymer (collagen gel) rod 150b showed neurites 152b that elongated randomly from the DRG 154b. The neurites were imaged by antibody staining (anti-neurofilament 200 KD).

EXAMPLE 6

Figure 13A:
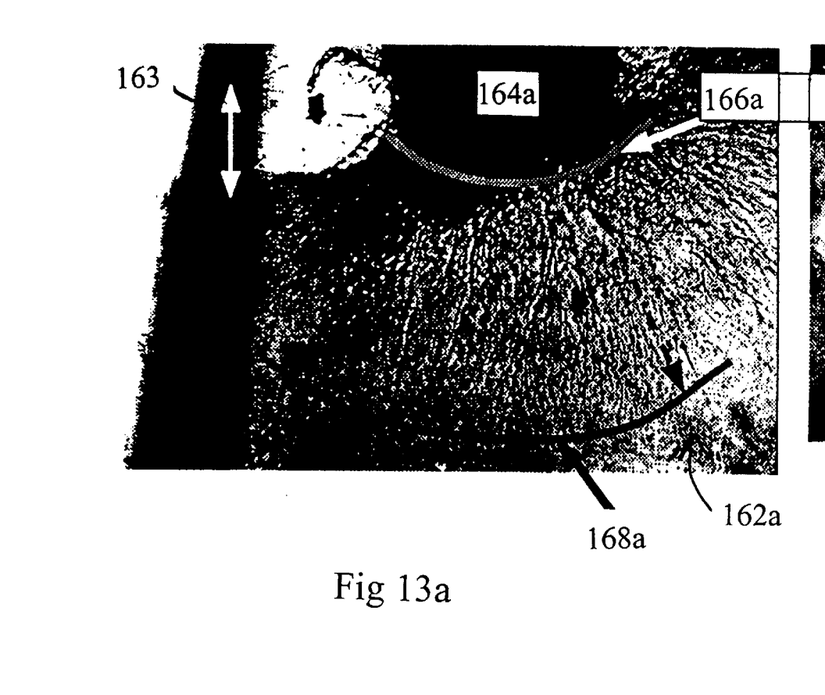
FIG. 13a is a perspective view of a dorsal root ganglia having been placed onto one end of an aligned biopolymer (collagen gel) rod of the present invention.
Figure 13B:
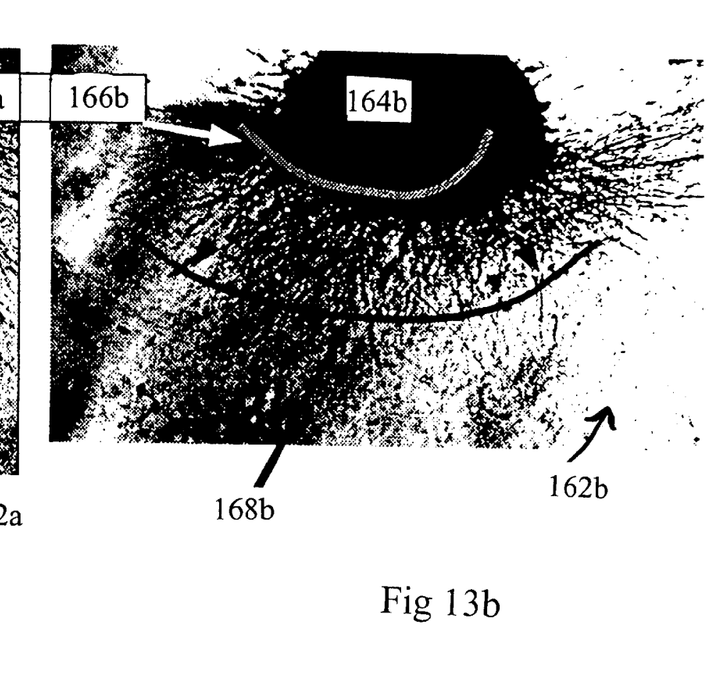
FIG. 13b is a perspective view of a dorsal root ganglia having been placed onto one end of a non-aligned (isotropic) biopolymer (collagen gel) rod.

A magnetically oriented biopolymer (collagen gel) rod was produced in accordance with the present invention, except polymer beads (as described above) were not included. An invasion assay was prepared as Dorsal Root Ganglia (DRG) was explanted from a day 12 chick embryo and placed on one flat end of the rod and incubated for two days for the case of a magnetically oriented rod, prepared in a 4.7 Tesla magnetic field (FIG. 13a). In FIGS. 13a and 13b, as seen along the longitudinal axes of the biopolymer (collagen gel) rods 162a, 162b the neurites from the DRG 164a, 164b have advanced from their respective neurite origins 166a, 166b. The leading edge of the DRG neurite front 168a in the aligned biopolymer rod 162a (having fibrils aligned in the direction of the arrow 163) has advanced further than the leading edge 168b of the DRG neurite front in the isotropic rod 162b (having non-aligned fibrils).

Figure 14A:
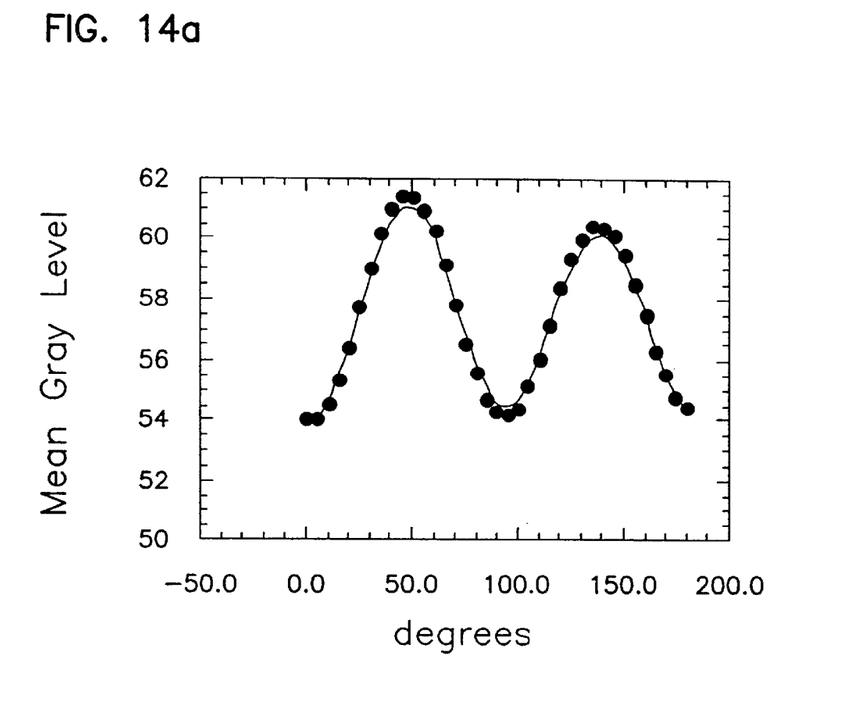
FIG. 14a is a birefringence diagram of light intensity (mean gray level) versus rotation (degrees) for the longitudinally aligned (oriented) biopolymer (collagen gel) rod of FIG. 13a of the present invention.
Figure 14B:
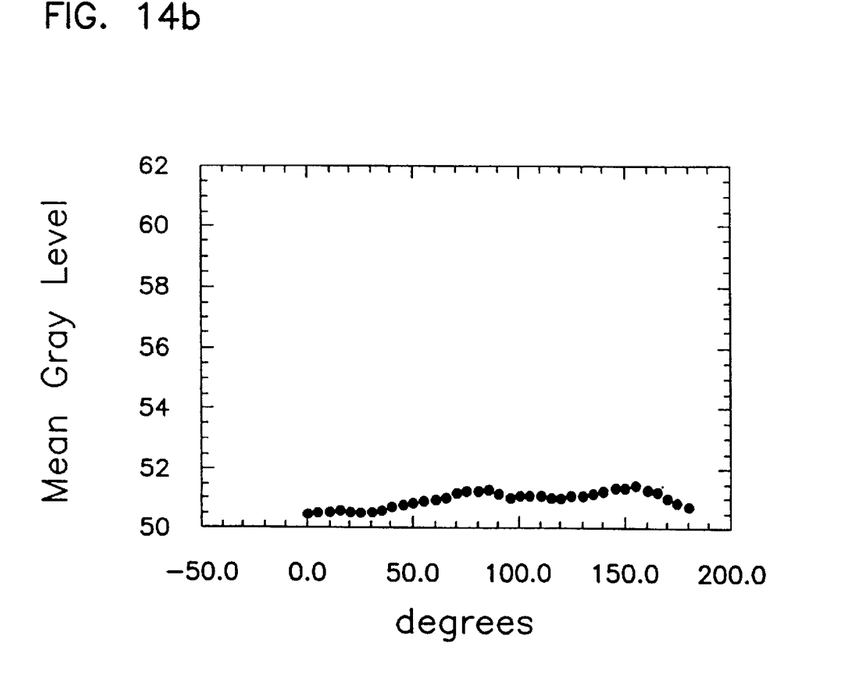
FIG. 14b is a birefringence diagram of light intensity (mean gray level) versus rotation (degrees) for the isotropic biopolymer (collagen gel) rod of FIG. 13b.

To confirm that the neurite advancement was due to magnetically aligned (oriented) collagen, the rods were analyzed in polarized light. As shown in FIG. 14a, the rod prepared in the 4.7 Tesla magnetic field exhibited strong birefringence ($47 \times 10^{-6}$), indicative of highly aligned collagen fibrils, whereas little or no birefringence was measured for the non-aligned fibril control (isotropic) rod, as shown in FIG. 14b.

While the invention has been described in connection with several embodiments, it will be understood that the invention is not limited to these embodiments. The invention is intended to cover all alternatives, modifications and equivalents as may be included within the spirit and scope thereof, as defined by the appended claims.

What is claimed is:

1. A method for promoting nerve regeneration comprising:
   a. providing a biopolymer rod having longitudinal and traverse dimensions and first and second ends, the rod being cylindrical and of a predetermined circumference, the rod having a body comprising a biopolymer, the biopolymer including fibrils, the fibrils aligning in a direction substantially parallel to the longitudinal dimension;
   b. positioning said biopolymer rod intermediate a first nerve ending and a second nerve ending; said first and second nerve ending formed by the severance of a nerve; and
   c. attaching said first end of said biopolymer rod to said first nerve ending and said second end of said biopolymer rod to said second nerve ending.

2. The method of claim 1, wherein the biopolymer is collagen.

3. The method of claim 1, wherein the biopolymer is Type I collagen.

4. The method of claim 1, wherein the biopolymer is fibrin.

5. The method of claim 1, wherein said biopolymer rod additionally comprises an outer casing including a biodegradable or bioresorbable polymer cylinder.

6. A method for providing nerve regeneration comprising:
   a. providing a biopolymer rod having longitudinal and traverse dimensions and first and second ends, the rod including a body comprising collagen, the collagen including fibrils, the fibrils being aligned in a direction substantially parallel to the longitudinal dimension;
   b. positioning said biopolymer rod intermediate a first nerve ending and a second nerve ending, said first and second nerve endings formed by the severance of a nerve; and
   c. attaching said first end of said biopolymer rod to said first nerve ending and said second end of said biopolymer rod to said second nerve ending.

7. The method of claim 6, wherein said biopolymer rod further comprising an outer casing comprising a biodegradable or bioresorbable polymer cylinder.

8. A method for providing nerve regeneration comprising:
   a. providing a biopolymer rod having longitudinal and traverse dimensions and first and second ends, the rod including a body comprising fibrin, the fibrin including fibrils, the fibrils being aligned in a direction substantially parallel to the longitudinal dimension;
   b. positioning said biopolymer rod intermediate a first nerve ending and a second nerve ending, said first and second nerve endings formed by the severance of a nerve; and
   c. attaching said first end of said biopolymer rod to said first nerve ending and said second end of said biopolymer rod to said second nerve ending.

9. The method of claim 8, wherein said biopolymer rod further comprising an outer casing comprising a biodegradable or bioresorbable polymer cylinder.

* * * * *

UNITED STATES PATENT AND TRADEMARK OFFICE
CERTIFICATE OF CORRECTION

PATENT NO. : 6,461,629 B1
DATED : October 8, 2002
INVENTOR(S) : Tranquillo et al.

It is certified that error appears in the above-identified patent and that said Letters Patent is hereby corrected as shown below:

Title page,
Item [56], References Cited, OTHER PUBLICATIONS, insert:
-- L'Heureux et al., "In Vitro Construction of a Human Blood Vessel from Cultured Vascular Cells: A Morphologic Study", Journal of Vascular Surgery, 17 (3): 499-509 (March 1993). --.

Column 9,
Line 29, "400ºC" should read -- 40ºC --

Column 11,
Line 43, "5W" should read -- 5% --

Signed and Sealed this

Twenty-seventh Day of May, 2003

JAMES E. ROGAN
*Director of the United States Patent and Trademark Office*